US012605310B2

(12) United States Patent
Shim et al.

(10) Patent No.: US 12,605,310 B2
(45) Date of Patent: Apr. 21, 2026

(54) NON-AQUEOUS DISPERSION, PREPARATION METHOD THEREFOR, AND COSMETIC COMPOSITION COMPRISING SAME

(71) Applicant: LG HOUSEHOLD & HEALTH CARE LTD., Seoul (KR)

(72) Inventors: Woo-Sun Shim, Seoul (KR); Hae-Seok Chae, Seoul (KR)

(73) Assignee: LG HOUSEHOLD & HEALTH CARE LTD., Seoul (KR)

(*) Notice: Subject to any disclaimer, the term of this patent is extended or adjusted under 35 U.S.C. 154(b) by 800 days.

(21) Appl. No.: 17/440,605

(22) PCT Filed: Oct. 8, 2019

(86) PCT No.: PCT/KR2019/013206
§ 371 (c)(1),
(2) Date: Sep. 17, 2021

(87) PCT Pub. No.: WO2020/189870
PCT Pub. Date: Sep. 24, 2020

(65) Prior Publication Data
US 2022/0160593 A1 May 26, 2022

(30) Foreign Application Priority Data
Mar. 20, 2019 (KR) ........................ 10-2019-0031964

(51) Int. Cl.
*A61K 8/04* (2006.01)
*A61K 8/31* (2006.01)
*A61K 8/81* (2006.01)
*A61Q 1/10* (2006.01)
*A61Q 19/00* (2006.01)

(52) U.S. Cl.
CPC .................. *A61K 8/04* (2013.01); *A61K 8/31* (2013.01); *A61K 8/8152* (2013.01); *A61Q 1/10* (2013.01); *A61Q 19/00* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 4,528,321 A | 7/1985 | Allen et al. | |
| 4,639,491 A * | 1/1987 | Kondo ...................... C08F 2/32 | |
| | | | 524/801 |
| 4,833,177 A | 5/1989 | Faler et al. | |
| 5,120,531 A | 6/1992 | Wells et al. | |
| 6,482,400 B1 | 11/2002 | Collin | |
| 9,096,755 B2 | 8/2015 | Chari et al. | |
| 10,071,046 B2 | 9/2018 | Portal et al. | |
| 2004/0126401 A1 | 7/2004 | Collin | |
| 2006/0093568 A1* | 5/2006 | Blin ...................... C08F 265/04 | |
| | | | 424/70.16 |
| 2007/0224151 A1 | 9/2007 | Mougin et al. | |
| 2010/0247470 A1 | 9/2010 | Friel et al. | |
| 2014/0364511 A1* | 12/2014 | Chari ...................... A61K 47/32 | |
| | | | 524/217 |
| 2015/0218297 A1* | 8/2015 | Naito ................... A61K 8/8158 | |
| | | | 510/123 |
| 2016/0015622 A1 | 1/2016 | Rafferty et al. | |

FOREIGN PATENT DOCUMENTS

| | | |
|---|---|---|
| CN | 105916479 A | 8/2016 |
| JP | 59-206403 A | 11/1984 |
| JP | 1-213303 A | 8/1989 |
| JP | 2002-322223 A | 11/2002 |
| JP | 2004-525101 A | 8/2004 |
| JP | 3577182 B2 | 10/2004 |
| JP | 2008-255014 A | 10/2008 |
| JP | 2018-24854 A | 2/2018 |
| JP | 2019-19150 A | 2/2019 |
| KR | 10-2001-0074873 A | 8/2001 |
| KR | 10-2011-0130451 A | 12/2011 |
| KR | 10-2017-0084291 A | 7/2017 |
| WO | WO 2010/117552 A2 | 10/2010 |
| WO | WO 2016/097361 A1 | 6/2016 |

OTHER PUBLICATIONS

Burke, John. 1984. "Solubility Parameters: Theory and Application." Book and Paper Group Annual 3: 13-58. (Year: 1984).*
Johnson W Jr, Bergfeld WF, Belsito DV, Hill RA, Klaassen CD, Liebler D, Marks JG Jr, Shank RC, Slaga TJ, Snyder PW, Andersen FA. Safety assessment of isoparaffins as used in cosmetics. Int J Toxicol. Nov.-Dec. 2012;31(6 Suppl):269S-95S. doi: 10.1177/1091581812463087. PMID: 23283704. (Year: 2012).*
Extended European Search Report for European Application No. 19920244.1, dated Apr. 18, 2023.
International Search Report for PCT/KR2019/013206 (PCT/ISA/210) mailed on Jan. 17, 2020.

* cited by examiner

*Primary Examiner* — Katherine Peebles
*Assistant Examiner* — Afua Bamfoaa Boateng
(74) *Attorney, Agent, or Firm* — Birch, Stewart, Kolasch & Birch, LLP

(57) ABSTRACT

The present invention relates to a non-aqueous dispersion, a preparation method therefor, and a cosmetic composition comprising same. The present invention can provide: a dispersion applicable to a coating agent and a cosmetic composition, which are well cleansed by even a large amount of water or a typical cleanser without an specific make-up remover or oil cleanser while having an excellent makeup lasting effect; a preparation method therefor, and a cosmetic composition comprising same.

7 Claims, 1 Drawing Sheet

| | 1min | 3min | 5min | 7min | 10min | 15min | 20min | WIPING TIME |
|---|---|---|---|---|---|---|---|---|
| PREP.EX.1 | | | | | | | | within 10 min. |
| PREP.EX.2 | | | | | | | | within 10 min. |
| PREP.EX.3 | | | | | | | | within 3 min. |
| PREP.EX.4 | | | | | | | | within 7 min. |
| PREP.EX.5 | | | | | | | | within 20 min. |
| PREP.EX.6 | | | | | | | | within 7 min. |
| COMP.EX.2 | | | | | | | | |
| O/W MASCARA | | | | | | | | within 7 min. |

NON-AQUEOUS DISPERSION, PREPARATION METHOD THEREFOR, AND COSMETIC COMPOSITION COMPRISING SAME

TECHNICAL FIELD

The present application claims priority to Korean Patent Application No. 10-2019-0031964 filed on Mar. 20, 2019 in the Republic of Korea, the disclosures of which are incorporated herein by reference. The present disclosure relates to a non-aqueous dispersion, a method for preparing the same and a cosmetic composition including the same.

BACKGROUND ART

Cosmetics for makeup, such as eye liner and mascara, use an oil-dispersed (non-aqueous dispersed) formulation or water-in-oil (W/O) formulation including various oil soluble coating agents in order to enhance makeup lasting effects, such as water resistance, curling effect and curl persistency. However, such cosmetics cannot wash off well with a general face washing agent or foam cleanser, and thus require the use of an oil cleanser or specific makeup remover. For this, eyelashes may be damaged, or skin irritation may occur, resulting in a difficulty in cleansing. Oil-in-water (O/W) formulations using a water soluble or water-dispersed coating agent may be used to improve the cleanability of such eye liner or mascara. In this case, cosmetic effects, such as curling effect and curl persistency, are degraded as compared to oil-dispersed formulations or W/O formulations using an oil soluble coating agent.

To overcome the above-mentioned problem, cosmetics for makeup using a non-aqueous polymer dispersion based on various copolymers have been known. For example, Japanese Patent No. 3577182 (Patent Document 1) discloses a cosmetic for makeup using volatile silicone, but the cosmetic shows a low evaporation rate and cannot be dried well during use. Japanese Patent Publication No. 2008-255014 (Patent Document 2) discloses an oil-based cosmetic using a non-aqueous polymer dispersion, but the cosmetic cannot wash off by cleansing with water and requires a separate face cleanser, such as oil.

Therefore, it is required to develop a coating agent and an oil-dispersed or W/O formulation containing the same which can wash off well with a large amount of water or general face cleanser without an specific makeup remover or oil cleanser.

DISCLOSURE

Technical Problem

The present disclosure is directed to providing a non-aqueous dispersion applicable to a coating agent and a cosmetic composition which are cleansed well with a large amount of water or general face cleanser with no need for an specific makeup remover or oil cleanser, while providing an excellent makeup lasting effect, and to providing a method for preparing the same, and a cosmetic composition including the same.

Technical Solution

To solve the above-mentioned technical problem, there are provided a non-aqueous dispersion comprising: a) a copolymer polymerized from at least one hydrophilic monomer selected from acryl and vinyl compounds with at least one hydrophobic monomer selected from alkyl acrylate, alkyl methacrylate, aromatic acrylate and aromatic methacrylate compounds; and b) a homopolymer polymerized from at least one hydrophilic monomer selected from acryl and vinyl compounds, a method for preparing the same, and a cosmetic composition including the same.

As used herein, the term 'hydrophilic' refers to a solubility parameter ($\delta$) of a homopolymer of 10.0 $(cal/cm^3)^{1/2}$ or more, and the term 'hydrophobic' refers to a solubility parameter ($\delta$) of a homopolymer of less than 10.0 $(cal/cm^3)^{1/2}$.

In one aspect of the present disclosure, there is provided a non-aqueous dispersion comprising: a) a copolymer polymerized from at least one hydrophilic monomer selected from acryl and vinyl compounds with at least one hydrophobic monomer selected from alkyl acrylate, alkyl methacrylate, aromatic acrylate and aromatic methacrylate compounds; and b) a homopolymer polymerized from at least one hydrophilic monomer selected from acryl and vinyl compounds.

In other words, according to the present disclosure, a non-aqueous dispersion including a hydrophilic homopolymer is provided by using a copolymer containing a hydrophilic monomer (acryl and/or vinyl compound) and a hydrophobic monomer (alkyl acrylate, alkyl methacrylate, aromatic acrylate and/or aromatic methacrylate compound) having high solubility in hydrocarbon-based oil, as a dispersion stabilizer, resulting in stable dispersion of the polymer in non-aqueous dispersion, particularly, in non-polar hydrocarbon-based oil (isododecane, isoparaffin, isohexadecane, or the like).

According to the present disclosure, the non-aqueous dispersion may be obtained by mixing a hydrophilic monomer in the presence of a copolymer containing a hydrophilic monomer and a hydrophobic monomer. In other words, it can be provided a hydrophilic non-aqueous dispersion which can be dispersed stably in hydrocarbon-based oil by using as a dispersion stabilizer a) the copolymer produced by the polymerization of at least one hydrophilic monomer selected from acryl and vinyl compounds with at least one hydrophobic monomer selected from alkyl acrylate, alkyl methacrylate, aromatic acrylate and aromatic methacrylate compounds, and mixing, in the presence of the copolymer, b) the homopolymer produced by the polymerization of at least one hydrophilic monomer selected from acryl and vinyl compounds to obtain a non-aqueous dispersion containing a homopolymer.

It is possible to prevent precipitation of a homopolymer of hydrophilic monomers not by mixing a homopolymer containing hydrophilic monomers and a hydrophilic-hydrophobic copolymer as separately prepared, but by mixing the homopolymer containing hydrophilic monomers in the polymerization solution of hydrophilic-hydrophobic copolymer. According to an embodiment of the present disclosure, it is possible to obtain a stable non-aqueous dispersion when a copolymer containing a large amount of hydrophobic monomers is polymerized first, and then secondary polymerization is carried out while adding hydrophilic monomers. It may be thought that the copolymer formed before the introduction of the homopolymer of hydrophilic monomers surrounds the homopolymer of hydrophilic monomers inside of an oil phase as an external phase (it's function is similar to that of an emulsifier), and thus prevents precipitation of the homopolymer to provide a stable non-aqueous dispersion. However, the present disclosure is not limited thereto. Such non-aqueous dispersion stably contains a homopolymer of water-soluble monomers, and thus can provide makeup persistency and easy cleanability with water.

Herein, the hydrophilic monomer used for a) copolymer and the hydrophilic monomer used for b) homopolymer may be the same or different. Particularly, a non-aqueous dispersion containing 'homopolymer and copolymer' can be obtained by using as a dispersion stabilizer a) copolymer of 'hydrophilic monomer/hydrophobic monomer' (also referred to as 'stabilizer copolymer' hereinafter), and further mixing hydrophilic monomers.

In this manner, it is possible to obtain a dispersion which comprises hydrophilic monomers in an amount of 50 wt % or more based on the total monomers and is dispersed stably in hydrocarbon-based oil. In addition, mascara containing the dispersion as a non-aqueous dispersion (oil dispersion) formulation or W/O formulation may be cleansed easily with a large amount of water or general face cleanser, while providing excellent cosmetic effects, such as water resistance and curl persistency.

Therefore, the total content of the hydrophilic monomers in the non-aqueous dispersion according to the present disclosure may be 50-90 wt %, particularly 50-80 wt %, and more particularly 55-75 wt %, based on the total weight of the monomers in the non-aqueous dispersion. Accordingly, the total content of the hydrophobic monomers may be 10-50 wt %, particularly 20-50 wt %, and more particularly 25-45 wt %, based on the total weight of the monomers in the non-aqueous dispersion.

The content of the hydrophilic monomer mixed when preparing the stabilizer copolymer according to the present disclosure may be 1-40 wt %, particularly 5-40 wt %, and more particularly 5-25 wt %, based on the total weight of the monomers in the corresponding stabilizer copolymer. When the content of the hydrophilic monomer is less than 1 wt %, the compatibility with the hydrophilic monomer (homopolymer) mixed during preparing the finished dispersion is poor, thereby making it difficult to stabilize the homopolymer. On the other hand, when the content of the hydrophilic monomer is larger than 40 wt %, the stabilizer copolymer itself shows poor solubility in the non-polar hydrocarbon-based oil used as a solvent, thereby making it difficult to stabilize the homopolymer.

The content of the hydrophobic monomer mixed during preparing the stabilizer copolymer according to the present disclosure may be 60-99 wt %, particularly 60-95 wt %, and more particularly 75-95 wt %, based on the total weight of the monomers in the corresponding stabilizer copolymer. When the content of the hydrophobic monomer is less than 60 wt %, the stabilizer copolymer itself shows poor solubility in the non-polar hydrocarbon-based oil used as a solvent, thereby making it difficult to stabilize the homopolymer. On the other hand, when the content of the hydrophobic monomer is larger than 99 wt %, the compatibility with the homopolymer is poor, thereby making it difficult to stabilize the homopolymer.

According to the present disclosure, the content of the homopolymer may be 10-80 wt %, particularly 30-70 wt %, and more particularly 45-65 wt %, based on the total weight of the monomers in the non-aqueous dispersion. When the content is less than 10 wt %, it may not provide a significant effect of improving cleanability, after the non-aqueous dispersion is applied to a mascara formulation. On the other hand, when the content is larger than 80 wt %, it may not obtain a finished dispersion containing the homopolymer dispersed stably in the non-polar hydrocarbon-based oil, and the homopolymer may be precipitated.

According to the present disclosure, the hydrophilic monomer may have a solubility parameter ($\delta$) of a homopolymer of 10-15 $(cal/cm^3)^{1/2}$, particularly 10-13 $(cal/cm^3)^{1/2}$, and more particularly 10-12 $(cal/cm^3)^{1/2}$. When the hydrophilic monomer has a solubility parameter higher than the above-defined range, it is difficult to obtain a dispersion dispersed stably in hydrocarbon-based oil. When the hydrophilic monomer has a solubility parameter lower than the above-defined range, it shows excessively low hydrophilicity, thereby making it difficult to provide an effect of improving cleanability.

According to the present disclosure, the hydrophobic monomer may have a solubility parameter ($\delta$) of a homopolymer of 5-9.5 $(cal/cm^3)^{1/2}$, particularly 7.5-9.5 $(cal/cm^3)^{1/2}$, and more particularly 8-9.5 $(cal/cm^3)^{1/2}$. When the hydrophobic monomer has a solubility parameter higher than the above-defined range, it is difficult to obtain a dispersion dispersed stably in hydrocarbon-based oil. When the hydrophobic monomer has a solubility parameter lower than the above-defined range, it is difficult to obtain a dispersion containing a hydrophilic polymer dispersed stably therein.

According to the present disclosure, the hydrophilic monomer is an acryl and/or vinyl compound, and may comprise 2-hydroxyethyl acrylate, 2-hydroxyethyl acrylate/methacrylate, acrylic acid, methacrylic acid, maleic acid, itaconic acid, polyoxyethylene acrylate/methacrylate, polyoxypropylene acrylate/methacrylate, glyceryl acrylate/methacrylate, acrylamide, methacrylamide, N-methyl acrylamide, N-methyl methacrylamide, N-ethyl acrylamide, N-ethyl methacrylamide, N-isopropyl acrylamide, N-isopropyl methacrylamide, N-butyl acrylamide, N-butyl methacrylamide, N,N-dimethylacrylamide, N,N-dimethyl methacrylamide, N,N-diethyl acrylamide, N,N-diethyl methacrylamide, N,N-dipropyl acrylamide, N,N-dipropyl methacrylamide, N,N-dibutyl acrylamide, N,N-dibutyl methacrylamide, N-methyl-N-ethyl acrylamide, N-methyl-N-ethyl methacrylamide, N-methyl-N-propyl acrylamide, N-methyl-N-propyl methacrylamide, N-methyl-N-butyl acrylamide, N-methyl-N-butyl methacrylamide, N-ethyl-N-propyl acrylamide, N-ethyl-N-propyl methacrylamide, N-ethyl-N-butyl acrylamide, N-ethyl-N-butyl methacrylamide, N-propyl-N-butyl acrylamide, N-propyl-N-butyl methacrylamide, N-methylol acrylamide, N-methylol methacrylamide, N-hydroxyethyl acrylamide, N-hydroxyethyl methacrylamide, N-methoxymethyl acrylamide, N-methoxymethyl methacrylamide, N-butoxymethyl acrylamide, N-butoxymethyl methacrylamide, N,N-dimethylaminopropyl acrylamide, N,N-dimethylaminopropyl methacrylamide, N,N-hydroxymethyl/ethyl acrylamide, N,N-hydroxymethyl/ethyl methacrylamide, acryloyl morpholine, N-vinyl pyrrolidone, N-vinyl-ε-caprolactam, N-vinyl formamide, N-vinyl acetamide, vinyl alcohol, vinyl sulfonic acid, styrene sulfonic acid, 2-acrylamido-2-methyl-1-propane sulfonic acid, diacetone acrylamide, methylacrylamide glycolate methyl ether, methyl methacrylamide glycolate methyl ether, N,N'-methylene bisacrylamide, or the like. Particularly, the hydrophilic monomer may be vinyl pyrrolidone and/or 2-hydroxyethyl acrylate. In this case, it is possible to obtain a dispersion having high stability and excellent water resistance and cleanability.

According to the present disclosure, the hydrophobic monomer is at least one selected from alkyl acrylate, alkyl methacrylate, aromatic acrylate and aromatic methacrylate compounds. The alkyl group in the acrylate/methacrylate compounds may comprise a $C_1$-$C_{20}$ linear, branched or cyclic alkyl group, and the aromatic acrylate/methacrylate may comprise aryl acrylate/methacrylate or arylalkyl acrylate/methacrylate. The aryl group may be a $C_6$-$C_{24}$ aryl group, and the alkyl group in the arylalkyl group may be a $C_1$-$C_{20}$ alkyl group. For example, the alkyl (meth)acrylate compounds may comprise methyl (meth)acrylate (acrylate and/or methacrylate is abbreviated as (meth)acrylate hereinafter), ethyl (meth)acrylate, propyl (meth)acrylate, isopropyl (meth)acrylate, butyl (meth)acrylate, isobutyl (meth)acrylate, sec-butyl (meth)acrylate, tert-butyl (meth)acrylate, 2-ethylhexyl (meth)acrylate, octyl (meth)acrylate, isooctyl (meth)acrylate, isononyl (meth)acrylate, isodecyl (meth)acrylate, isoundecyl (meth)acrylate, lauryl (meth)acrylate, isododecyl (meth)acrylate, stearyl (meth)acrylate, isostearyl (meth)acrylate, isotridecyl (meth)acrylate, myristyl (meth)acrylate, cetyl (meth)acrylate, isooctadecyl (meth)acrylate, oleyl (meth)acrylate, eicosyl (meth)acrylate, cyclopentyl (meth)acrylate, cyclohexyl (meth)acrylate, butylcyclohexyl (meth)acrylate, dicyclopentanyl (meth)acrylate, dicylopentenyl (meth)acrylate, dicyclopentenyloxyethyl (meth)acrylate, isoboronyl (meth)acrylate, 2-phenoxy (meth)acrylate, 2-phenoxyethyl (meth)acrylate, nonylphenol acrylate, cyclic trimethylolpropane formal acrylate, tetrafurfuryl (meth) acrylate, oxazolidone (meth)acrylate, glycerol (meth)acrylate, N-acryloyloxyethyl hexahydrophthalimide, styrene, α-methylstyrene, β-methylstyrene, 4-methylstyrene, or the like. Particularly, the hydrophobic monomer may be at least one selected from n-butyl acrylate, n-butyl methacrylate, tert-butyl acrylate, tert-butyl methacrylate, lauryl methacrylate and stearyl methacrylate. In this case, it is possible to obtain a dispersion having high stability and excellent water resistance and cleanability.

According to the present disclosure, the hydrocarbon-based oil is non-polar oil, preferably. Particularly, the hydrocarbon-based oil may be $C_{16}$-$C_{18}$ hydrocarbon-based oil, more particularly $C_{10}$-$C_{16}$ hydrocarbon-based oil, such as dodecane, isododecane, isoparaffin, or the like. In this case, it is possible to obtain a dispersion having high stability and excellent water resistance and cleanability.

In another aspect of the present disclosure, there is provided a method for preparing a non-aqueous dispersion, comprising the steps of: S1) a first step of mixing and polymerizing at least one hydrophilic monomer selected from acryl and vinyl compounds with at least one hydrophobic monomer selected from alkyl acrylate, alkyl methacrylate, aromatic acrylate and aromatic methacrylate compounds; and S2) a second step of mixing and polymerizing at least one hydrophilic monomer selected from acryl and vinyl compounds in the presence of the polymerized product of the first step. It is possible to obtain a stable non-aqueous dispersion, while preventing precipitation of the homopolymer of the hydrophilic monomer, by carrying out the first step and the second step sequentially. In addition, the stabilized non-aqueous dispersion obtained by the method according to an embodiment of the present disclosure can provide a makeup lasting effect and easy cleanability with water.

The non-aqueous dispersion according to the present disclosure may be obtained through the radical polymerization of the monomers for forming the dispersion in an organic solvent by using a radical initiator.

The method for preparing a non-aqueous dispersion according to the present disclosure may further comprise hydrocarbon-based oil and a radical initiator in step S1), and may further comprise a radical initiator in step S2). Therefore, the non-aqueous dispersion according to the present disclosure may be obtained by preparing a copolymer through the first step S1) of mixing and polymerizing the hydrophilic monomer, hydrophobic monomer, hydrocarbon-based oil and the radical initiator (step for preparing dispersion stabilizer copolymer), and then carrying out the second step S2) of mixing and polymerizing the radical initiator and hydrophilic monomer in the presence of the polymerized product of the first step (step for stabilizing for homopolymer).

The hydrophilic monomer is the same as described above. Therefore, the homopolymer of the hydrophilic monomer according to the present disclosure may have a solubility parameter (δ) of a homopolymer of 10-15 $(cal/cm^3)^{1/2}$, particularly 10-13 $(cal/cm^3)^{1/2}$.

Particularly, the hydrophilic monomer may be vinyl pyrrolidone. In this case, it is possible to obtain a dispersion having high stability and excellent water resistance and cleanability.

The hydrophilic monomer used in step S1) (step for preparing dispersion stabilizer copolymer) and the hydrophilic monomer used in step S2) (step for stabilizing homopolymer) may be the same or different. Particularly, the hydrophilic monomers used in steps S1) and S2) may be vinyl pyrrolidone.

The hydrophobic monomer is the same as described above. Therefore, the homopolymer of the hydrophobic monomer according to the present disclosure may have a solubility parameter (δ) of a homopolymer of 5-9.5 $(cal/cm^3)^{1/2}$, particularly 7-9.5 $(cal/cm^3)^{1/2}$.

Particularly, the hydrophobic monomer may be at least one selected from n-butyl acrylate, n-butyl methacrylate, tert-butyl acrylate, tert-butyl methacrylate, lauryl methacrylate and stearyl methacrylate. In this case, it is possible to obtain a dispersion having high stability and excellent water resistance and cleanability.

The content of the hydrophilic monomer mixed in step S1) (step for preparing dispersion stabilizer copolymer) according to the present disclosure may be 1-40 wt %, particularly 5-40 wt %, and more particularly 5-25 wt %, based on the total weight of the monomers mixed in step S1). When the content of the hydrophilic monomer is less than 1 wt %, the compatibility with the homopolymer is poor, thereby making it difficult to stabilize the homopolymer. On the other hand, when the content of the hydrophilic monomer is larger than 40 wt %, the solubility in the non-polar hydrocarbon-based oil is poor, thereby making it difficult to stabilize the homopolymer.

The content of the hydrophobic monomer mixed in step S1) (step for preparing dispersion stabilizer copolymer) according to the present disclosure may be 60-99 wt %, particularly 60-95 wt %, and more particularly 75-95 wt %, based on the total weight of the monomers mixed in step S1). When the content of the hydrophobic monomer is less than 60 wt %, the stabilizer copolymer itself shows low solubility in the non-polar hydrocarbon-based oil, thereby causing precipitation or making it difficult to stabilize the homopolymer. On the other hand, when the content of the hydrophilic monomer is larger than 99 wt %, the compatibility with the homopolymer is poor, thereby making it difficult to stabilize the homopolymer, resulting in precipitation of the homopolymer.

The total content of the hydrophilic monomer in the non-aqueous dispersion obtained according to the present disclosure may be 50-90 wt %, particularly 50-80 wt %, and more particularly 55-75 wt %, based on the total weight of the monomers in the non-aqueous dispersion. Therefore, the total content of the hydrophobic monomer in the non-aqueous dispersion obtained according to the present disclosure may be 10-50 wt %, particularly 20-50 wt %, and more particularly 25-45 wt %, based on the total weight of the monomers in the non-aqueous dispersion.

According to the present disclosure, the content of the hydrophilic monomer mixed in step S2) (step for stabilizing homopolymer) may be 10-80 wt %, particularly 30-70 wt %, and more particularly 45-65 wt %, based on the total weight of the monomers mixed during preparing the non-aqueous dispersion. When the content is less than 10 wt %, it may not provide a significant effect of improving cleanability, after the non-aqueous dispersion is applied to a mascara formulation. On the other hand, when the content is larger than 80 wt %, it may not obtain a finished dispersion containing the homopolymer dispersed stably in non-polar hydrocarbon-based oil, and the homopolymer is precipitated.

According to the present disclosure, the hydrocarbon-based oil is the same as described above. Particularly, the hydrocarbon-based oil may be $C_{16}$-$C_{18}$ hydrocarbon-based oil, such as dodecane, isododecane, isoparaffin, or the like. In this case, it is possible to obtain a dispersion having high stability and excellent water resistance and cleanability.

According to the present disclosure, the radical initiator is the same as described above. Particularly, the radical initiator may be an azo compound or an organic peroxide compound. Particular examples of the azo compound comprise 2,2'-azobisisobutyronitrile, 2,2'-azobis(-methoxy-2,4-dimethylvaleronitrile), 2,2'-azobis(2,4-dimethylvaleronitrile), dimethyl-2,2'-azobis(-methylpropionate), 2,2'-azobis(2-methylbutyronitrile), 2,2'-azobis[N-(2-propenyl)-2-methoxypropionamide, 2,2'-azobis(N-butyl-2-methylpropionamide), 2,2'-azobis(N-cyclohexyl-2-methylpropionamide), or the like. Particular examples of the organic peroxide compound comprise lauroyl peroxide, octanoyl peroxide, benzoyl peroxide, cumene hydroperoxide, dicumyl peroxide, t-butyl hydroperoxide, cumyl peroxy neodecanoate, or the like.

According to the present disclosure, the radical initiator may be used in an amount of 0.01-10 wt %, particularly 0.1-5 wt %, and more particularly 0.5-2 wt %, based on the total weight of the monomers in the finished dispersion. When the content is less than 0.01 wt %, the reaction may be delayed or the conversion rate into a polymer may be low. On the other hand, when the content is larger than 10 wt %, the polymer has an excessively low molecular weight and may not be able to show coating properties, when applying the formulation.

The content of the radical initiator mixed in step S1) may be 0.01-10 wt %, particularly 0.1-5 wt %, and more particularly 0.5-2 wt %, based on the total weight of the monomers mixed in step S1).

The content of the radical initiator mixed in step S2) may be 0.01-10 wt %, particularly 0.1-5 wt %, and more particularly 0.5-2 wt %, based on the total weight of the monomers mixed in step S2).

The method according to the present disclosure may be carried out at a temperature for a time suitable for the preparation and stabilization of the dispersion. Therefore, according to the present disclosure, step S1) may be carried out at 70-95° C. for 4-10 hours, particularly at 75-90° C. for 5-8 hours, and more particularly, at 80-85° C. for 5.5-7 hours.

According to the present disclosure, step S2) may be carried out at the same temperature as step S1), or at a temperature maintained within a difference of ±10%. Therefore, according to the present disclosure, step S2) may be carried out at 70-95° C. for 5-24 hours, particularly at 75-90° C. for 7-18 hours, and more particularly, at 80-85° C. for 10-15 hours.

In still another aspect of the present disclosure, there is provided a non-aqueous dispersion obtained by the above-described method.

In still another aspect of the present disclosure, there is provided a cosmetic composition including the above-described non-aqueous dispersion.

According to the present disclosure, the cosmetic composition may be a formulation selected from day cream, powder cream, face powder (loose or pressed type), rouge, cream makeup, eye shadow, mascara, eye liner, eyebrow pencil, lipstick, lip gloss, lip contour pencil and nail varnish.

According to the present disclosure, the cosmetic composition may be any one composition selected from water-in-oil type and oil-dispersed type compositions.

To provide the cosmetic composition, conventional cosmetic ingredients may be contained, and particular examples thereof may comprise wax, organically modified clay compounds, dextrin fatty acid esters, aprotic polar solvents, or the like.

The composition according to the present disclosure may comprise at least one wax. Herein, 'wax' means an lipophilic compound which is solid at room temperature (25° C.) and undergoes a reversible solid/liquid phase change. The wax may comprise hydrocarbon-based wax, fluoro-wax and silicone wax, and may be derived from plants, animals, minerals and synthetic materials.

For example, the hydrocarbon-based wax may comprise vegetable wax, such as carnauba wax, candelilla wax or rice bran wax, animal wax, such as bees wax, microcrystalline wax, paraffin wax, wax obtained through the Fisher-Tropsch synthesis, wax copolymers, or the like. The hydrocarbon-based wax may also comprise hydrogenated jojoba oil, sunflower oil, castor oil and lanolin oil obtained through the catalytic hydrogenation of animal or vegetable oil containing a linear or branched $C_8$-$C_{22}$ aliphatic chain.

The silicone wax may comprise $C_{16}$-$C_{45}$ alkyl or alkoxy dimethicone, polypropylsilsesquioxane wax, or the like.

The content of the wax in the composition according to the present disclosure may be 0.1-40 wt %, particularly 1-30 wt %, and more particularly 3-20 wt %. When the content is less than 0.1 wt %, it may not obtain good curling capability. On the other hand, when the content is larger than 40 wt %, the makeup effect is degraded and the cleanability with a general face cleanser is also degraded.

The composition according to the present disclosure may comprise at least one organically modified clay compound. The composition may provide improved long-term stability and excellent makeup effect, water repellency and oil repellency by using the organically modified clay compound.

The content of the organically modified clay compound in the composition according to the present disclosure may be 0.1-20 wt %, particularly 0.5-10 wt %, and more particularly 1-8 wt %. When the content is less than 0.1 wt %, it may not realize mascara viscosity, resulting in degradation of usability. On the other hand, when the content is larger than 20 wt %, mascara viscosity is excessively high, resulting in degradation of a soft feeling of use.

Particular examples of the organically modified clay compound may comprise compounds obtained by modifying natural or synthetic clay minerals, such as montmorillonite, beidellite, nontrinite, saponite and hectorite, with a quaternary ammonium type cationic surfactant, and non-limiting examples thereof may comprise dimethylalkylammonium hectorite, benzyldimethylstearylammonium hectorite, dimethyldistearylammonium hectorite, or the like.

The composition according to the present disclosure may comprise at least one dextrin fatty acid ester. It is possible to provide improved long-term stability and to contribute to usability and makeup effect by using the dextrin fatty acid ester.

The content of the dextrin fatty acid ester in the composition according to the present disclosure may be 0.1-30 wt %, particularly 0.5-20 wt %, and more particularly 1-15 wt %. When the content is less than 0.1 wt %, it may not improve the formulation stability. On the other hand, when the content is larger than 30 wt %, the makeup effect is degraded significantly.

Particular examples of the dextrin fatty acid ester comprise dextrin myristate, dextrin palmitate, dextrin stearate, dextrin isostearate, dextrin palmitate/ethyl hexanoate, or the like, but are not limited thereto.

The composition according to the present disclosure may comprise at least one aprotic polar solvent. The aprotic polar solvent contributes to curl persistency and a soft feeling of use, and the content of the aprotic polar solvent may be 0.1-15 wt %, particularly 0.5-10 wt %, and more particularly 0.5-5 wt %. When the content is less than 0.1 wt %, the curling effect is degraded. When the content is larger than 15 wt %, it may not provide a soft feeling of use, resulting in degradation of the usability.

Particular examples of the aprotic polar solvent comprise propylene carbonate, triethyl citrate, diisostearyl maleate, polyglyceryl 2-isostearate, ethylhexylhydroxystearate, or the like, but are not limited thereto.

The composition according to the present disclosure may further comprise other ingredients used conventionally in cosmetics or medicines, with the proviso that the composition provides an intrinsic effect such as water resistance, oil resistance and a good adhesion and an excellent effect of make-up.

For example, the composition may further comprise oil, surfactants, purified water, polyhydric alcohols (glycerin, propylene glycol, 1,3-butylene glycol, or the like), organic powder, inorganic powder, UV absorbing agents, preservatives, defoaming agents, antibacterial agents, antioxidants, cosmetic ingredients, fragrance, thickeners, gelling agents, metal soap, water soluble polymers, oil soluble polymers, fibers (nylon, rayon, or the like), pigments, pearl agents, or the like.

The content of the dispersion in the cosmetic composition according to the present disclosure may be 1-50 wt %, particularly 2-30 wt %, and more particularly 5-25 wt %, based on the total weight of the composition. Within the above-defined range, it is possible to provide excellent makeup effects, such as cleanability, water resistance, oil resistance and curling effect, and excellent usability or stability as a commercialized product.

Advantageous Effects

According to the present disclosure, it is possible to provide a dispersion applicable to a coating agent and a cosmetic composition which wash off well with a large amount of water or general face cleanser with no need for an specific makeup remover or oil cleanser, while providing an excellent makeup lasting effect, and a method for preparing the same.

DESCRIPTION OF DRAWINGS

FIG. 1 shows the cleanability test result of the cosmetic composition according to an embodiment of the present disclosure.

MODE FOR DISCLOSURE

Hereinafter, the present disclosure will be explained in more detail with reference to examples. However, the following examples are for illustrative purposes only and not intended to limit the scope of this disclosure.

To obtain the dispersion containing a hydrophilic polymer dispersed stably in non-polar hydrocarbon-based oil, a hydrophilic monomer and hydrophobic monomer are polymerized first in a nonpolar solvent by using a thermal initiator at 85° C. for 6 hours through radical polymerization to obtain a copolymer. To the resultant copolymer solution, a solution containing a hydrophilic monomer and an initiator is added, while maintaining the temperature at 85° C. Then, reaction was carried out for 12 hours to obtain an oil dispersion containing the homopolymer of the hydrophilic monomer dispersed stably in non-polar hydrocarbon-based oil.

1. Preparation of Polymer and Dispersion According to the Present Disclosure

Example 1

First, 300 g of isododecane as non-polar hydrocarbon-based oil, 10 g of vinyl pyrrolidone as a hydrophilic monomer, 50 g of n-butyl acrylate and 40 g of stearyl methacrylate as hydrophobic monomers were introduced to a reactor equipped with a condenser, nitrogen injector, thermometer and an agitator, mixed homogeneously, and then warmed to 85° C. Next, 1 g of 2,2'-azobisisobutyronitrile was introduced thereto as a radical initiator and reaction was carried out for 6 hours to obtain a copolymer (first step). After the reaction, a mixed solution containing 100 g of vinyl pyrrolidone as a hydrophilic monomer and 1 g of 2,2'-azobisisobutyronitrile as a radical initiator was introduced gradually to carry out reaction at 85° C. for 12 hours (second step).

In this manner, a copolymer of vinyl pyrrolidone:n-butyl acrylate:stearyl methacrylate (1:5:4, weight ratio) was obtained from the first step, and a hydrophilic polymer oil dispersion of polyvinyl pyrrolidone:copolymer of the first step (5:5, weight ratio) was obtained from the second step.

The polymer particles in the resultant finished oil dispersion had a size of 87 nm and were dispersed stably in isododecane. In addition, the total content of the hydrophilic monomer in the finished polymer was 55%.

Example 2

Under the same synthesis condition as Example 1, 8 g of vinyl pyrrolidone as a hydrophilic monomer, 40 g of n-butyl acrylate and 32 g of stearyl methacrylate as hydrophobic monomers, and 0.8 g of 2,2'-azobisisobutyronitrile as a radical initiator were introduced to obtain a copolymer (first step). Then, after the reaction, 120 g of vinyl pyrrolidone as a hydrophilic monomer and 1.2 g of 2,2'-azobisisobutyronitrile as a radical initiator were introduced (second step).

In this manner, a copolymer of vinyl pyrrolidone:n-butyl acrylate:stearyl methacrylate (1:5:4, weight ratio) was obtained from the first step, and a hydrophilic polymer oil dispersion of polyvinyl pyrrolidone:copolymer of the first step (3:2, weight ratio) was obtained from the second step.

The polymer particles in the resultant finished oil dispersion had a size of 88 nm and were dispersed stably in isododecane. In addition, the total content of the hydrophilic monomer in the finished polymer was 64%.

Example 3

Under the same synthesis condition as Example 1, 6 g of vinyl pyrrolidone as a hydrophilic monomer, 30 g of n-butyl acrylate and 24 g of stearyl methacrylate as hydrophobic monomers, and 0.6 g of 2,2'-azobisisobutyronitrile as a radical initiator were introduced to obtain a copolymer (first step). Then, after the reaction, 140 g of vinyl pyrrolidone as a hydrophilic monomer and 1.4 g of 2,2'-azobisisobutyronitrile as a radical initiator were introduced (second step).

In this manner, a copolymer of vinyl pyrrolidone:n-butyl acrylate:stearyl methacrylate (1:5:4, weight ratio) was obtained from the first step, and a hydrophilic polymer oil dispersion of polyvinyl pyrrolidone:copolymer of the first step (7:3, weight ratio) was obtained from the second step.

The polymer particles in the resultant finished oil dispersion had a size of 87 nm and were dispersed stably in isododecane. In addition, the total content of the hydrophilic monomer in the finished polymer was 73%.

Example 4

Under the same synthesis condition as Example 1, 20 g of vinyl pyrrolidone as a hydrophilic monomer, 40 g of n-butyl acrylate and 40 g of stearyl methacrylate as hydrophobic monomers, and 1 g of 2,2'-azobisisobutyronitrile as a radical initiator were introduced to obtain a copolymer (first step). Then, after the reaction, 100 g of vinyl pyrrolidone as a hydrophilic monomer and 1 g of 2,2'-azobisisobutyronitrile as a radical initiator were introduced (second step).

In this manner, a copolymer of vinyl pyrrolidone:n-butyl acrylate:stearyl methacrylate (1:2:2, weight ratio) was obtained from the first step, and a hydrophilic polymer oil dispersion of polyvinyl pyrrolidone:copolymer of the first step (1:1, weight ratio) was obtained from the second step.

The polymer particles in the resultant finished oil dispersion had a size of 86 nm and were dispersed stably in isododecane. In addition, the total content of the hydrophilic monomer in the finished polymer was 60%.

Example 5

Under the same synthesis condition as Example 1, 30 g of vinyl pyrrolidone as a hydrophilic monomer, 30 g of n-butyl acrylate and 40 g of stearyl methacrylate as hydrophobic monomers, and 1 g of 2,2'-azobisisobutyronitrile as a radical initiator were introduced to obtain a copolymer (first step).

Then, after the reaction, 100 g of vinyl pyrrolidone as a hydrophilic monomer and 1 g of 2,2'-azobisisobutyronitrile as a radical initiator were introduced (second step).

In this manner, a copolymer of vinyl pyrrolidone:n-butyl acrylate:stearyl methacrylate (3:3:4, weight ratio) was obtained from the first step, and a hydrophilic polymer oil dispersion of polyvinyl pyrrolidone:copolymer of the first step (1:1, weight ratio) was obtained from the second step.

The polymer particles in the resultant finished oil dispersion had a size of 74 nm and were dispersed stably in isododecane. In addition, the total content of the hydrophilic monomer in the finished polymer was 65%.

Example 6

A dispersion was prepared under the same synthesis condition as Example 1, except that 2-hydroxyethyl acrylate was used as a hydrophilic monomer instead of vinyl pyrrolidone.

In this manner, a copolymer of 2-hydroxyethyl acrylate:n-butyl acrylate:stearyl methacrylate (1:5:4, weight ratio) was obtained from the first step, and a hydrophilic polymer oil dispersion of poly(2-hydroxyethyl acrylate):copolymer of the first step (1:1, weight ratio) was obtained from the second step.

The polymer particles in the resultant finished oil dispersion had a size of 98 nm and were dispersed stably in isododecane. In addition, the total content of the hydrophilic monomer in the finished polymer was 55%.

Comparative Example 1

A copolymer containing vinyl pyrrolidone as a hydrophilic monomer at the same content of 55% as Example 1 by using the same apparatus and temperature as Example 1 was prepared. Particularly, 300 g of isododecane, 110 g of vinyl pyrrolidone as a hydrophilic monomer, and 50 g of n-butyl acrylate and 40 g of stearyl methacrylate as hydrophobic monomers were introduced to the reactor, mixed homogeneously, and warmed to 85° C. In addition, 2 g of 2,2'-azobisisobutyronitrile was introduced as a radical initiator, and reaction was carried out for 12 hours to obtain a copolymer.

However, the resultant copolymer showed excessively low compatibility with hydrocarbon-based oil and was precipitated. Therefore, it was not possible to obtain a stably dispersed oil dispersion.

TABLE 1

| | | | Comp Ex. 1 | Ex. 1 | Ex. 2 | Ex. 3 | Ex. 4 | Ex. 5 | Ex. 6 |
|---|---|---|---|---|---|---|---|---|---|
| Hydrophilic monomer (g) | Vinyl pyrrolidone (VP) | Step 1 | 110 | 10 | 8 | 6 | 20 | 30 | — |
| | | Step 2 | — | 100 | 120 | 140 | 100 | 100 | — |
| | 2-Hydroxyethyl acrylate (2-HEA) | Step 1 | — | — | — | — | — | — | 10 |
| | | Step 2 | — | — | — | — | — | — | 100 |
| Hydrophobic monomer | n-Butyl acrylate (n-BA) | | 50 | 50 | 40 | 30 | 40 | 30 | 50 |
| | Stearyl methacrylate (SMA) | | 40 | 40 | 32 | 24 | 40 | 40 | 40 |
| Radical initiator | 2,2'-azobis isobutyronitrile | Step 1 | 2 | 1 | 0.8 | 0.6 | 1 | 1 | 1 |
| | | Step 2 | — | 1 | 1.2 | 1.4 | 1 | 1 | 1 |
| Solvent | Isododecane | | 300 | 300 | 300 | 300 | 300 | 300 | 300 |
| Particle size | | | Precipitated | 87 nm | 88 nm | 87 nm | 86 nm | 74 nm | 98 nm |

TABLE 1-continued

| | | Comp Ex. 1 | Ex. 1 | Ex. 2 | Ex. 3 | Ex. 4 | Ex. 5 | Ex. 6 |
|---|---|---|---|---|---|---|---|---|
| Weight ratio | Hydrophilic monomer of step 1:n-BA:SMA | — | 1:5:4 | 1:5:4 | 1:5:4 | 1:2:2 | 3:3:4 | 1:5:4 |
| | Homopolymer of step 2:copolymer of step 1 | — | 1:1 | 3:2 | 7:3 | 1:1 | 1:1 | 1:1 |
| Ratio of hydrophilic monomer based on the total weight of polymer | | 55 | 55 | 64 | 73 | 60 | 65 | 55 |

2. Preparation of Mascara

Mascara according to each of Preparation Examples and Comparative Example having the composition as shown in the following Table 2 was prepared, and the quality thereof was evaluated.

1) Ingredients 3-9 and a part of Ingredient 10 were mixed, heated and dispersed homogeneously.

2) The balance of Ingredient 10 and Ingredients 11-14 were mixed, heated and dispersed homogeneously.

3) The product of 2) was added to the product of 1) and dispersed homogeneously therein, and then Ingredients 1 and 2 were added thereto, followed by cooling, to obtain each mascara.

TABLE 2

| | (Wt %) | Prep. Ex. 1 | Prep. Ex. 2 | Prep. Ex. 3 | Prep. Ex. 4 | Prep. Ex. 5 | Prep. Ex. 6 | Comp. Ex. 2 |
|---|---|---|---|---|---|---|---|---|
| 1 | Ex. 1 | 25 | — | — | — | — | — | — |
| | Ex. 2 | — | 25 | — | — | — | — | — |
| | Ex. 3 | — | — | 25 | — | — | — | — |
| | Ex. 4 | — | — | — | 25 | — | — | — |
| | Ex. 5 | — | — | — | — | 25 | — | — |
| | Ex. 6 | — | — | — | — | — | 25 | — |
| 2 | Trimethylsiloxy silicate | — | — | — | — | — | — | 10 |
| 3 | Ceresin | 5 | 5 | 5 | 5 | 5 | 5 | 5 |
| 4 | Microcrystalline wax | 5 | 5 | 5 | 5 | 5 | 5 | 5 |
| 5 | Bees wax | 2 | 2 | 2 | 2 | 2 | 2 | 2 |
| 6 | Carnauba wax | 1 | 1 | 1 | 1 | 1 | 1 | 1 |
| 7 | Dextrin palmitate/ethyl hexanoate | 3 | 3 | 3 | 3 | 3 | 3 | 3 |
| 8 | Propylene carbonate | 1 | 1 | 1 | 1 | 1 | 1 | 1 |
| 9 | Triethylhexanoin | 2 | 2 | 2 | 2 | 2 | 2 | 2 |
| 10 | Isododecane | 36.7 | 36.7 | 36.7 | 36.7 | 36.7 | 36.7 | 51.7 |
| 11 | Disteardimonium hectorite | 3 | 3 | 3 | 3 | 3 | 3 | 3 |
| 12 | Iron oxide | 6 | 6 | 6 | 6 | 6 | 6 | 6 |
| 13 | Talc | 10 | 10 | 10 | 10 | 10 | 10 | 10 |
| 14 | simethicone | 0.3 | 0.3 | 0.3 | 0.3 | 0.3 | 0.3 | 0.3 |

3. Cleanability Test Results of Mascara O/W Formulation and Examples

1) Cleanability of Mascara

Each mascara was applied onto a transparent film to a thickness of 100 μm and dried at room temperature (23° C., 65% RH) for 12 hours to obtain a mascara coating film. Then, purified water at room temperature (23° C.) was dropped to the mascara coating film and wiped off after the lapse of a predetermined time (1 minute, 3 minutes, 7 minutes, 10 minutes, 15 minutes, and 20 minutes). The cleanability of each mascara was evaluated according to the following criteria.

TABLE 3

| ◎ | Coating film is swelled and wiped off within 7 minutes. |
|---|---|
| ○ | Coating film is swelled and wiped off within more than 7 minutes to 10 minutes. |
| Δ | Coating film is swelled and wiped off within more than 10 minutes to 15 minutes. |
| X | Coating film shows no change in appearance or is not removed at all even within 15 minutes. |

In the evaluation criteria, ◎ and ○ corresponding to the results similar to the cleanability test result of O/W mascara are judged as passed.

2) Water Resistance of Mascara

Each mascara was applied onto a transparent film to a thickness of 100 μm and dried at room temperature (23° C., 65% RH) for 12 hours, and then the contact angle was determined. The contact angle of each mascara was evaluated according to the following criteria.

TABLE 4

| ◎ | Mascara coating film has a contact angle of 100° or more. |
|---|---|
| ○ | Mascara coating film has a contact angle of 80° or more. |
| Δ | Mascara coating film has a contact angle of 80-40°. |
| X | Mascara coating film has a contact angle of 40° or less. |

In the evaluation criteria, ◎ and ○ are judged as passed.

3) Usability of Mascara

The usability of each mascara was tested by 20 professional panels (25-50 aged). Each mascara was evaluated in terms of the applicability (how smoothly each mascara is applied), makeup effect, smearing (how easily each mascara is smeared by sweat, water and sebum 6 hours after the application), makeup lasting effect and cleanability according to the following criteria with a 5-point scale, and the result is expressed by the average value.

TABLE 5

| ◎ | Average of 4.5 or more |
|---|---|
| ○ | Average of less than 4.5 and 3.5 or more |
| Δ | Average of less than 3.5 and 2.5 or more |
| X | Average of less than 2.5 |

4) Test Results

The test results are shown in the following Table 6. The test result of 3.1) mascara cleanability is shown in FIG. 1 as a photographic image.

TABLE 6

| | Prep. Ex. 1 | Prep. Ex. 2 | Prep. Ex. 3 | Prep. Ex. 4 | Prep. Ex. 5 | Prep. Ex. 6 | Comp. Ex. 2 |
|---|---|---|---|---|---|---|---|
| Cleanability of mascara | ○ | ○ | ◎ | ◎ | X | ◎ | X |
| Water resistance of mascara | ◎ | ◎ | △ | ◎ | ◎ | ○ | ◎ |
| Evaluation of usability of mascara — 1) Applicability | ○ | ○ | △ | ◎ | △ | ◎ | ○ |
| 2) Makeup effect | ○ | ○ | ○ | ○ | ○ | ○ | ○ |
| 3) Smearing | ○ | ○ | ◎ | ◎ | ○ | ◎ | X |
| 4) Makeup lasting effect | ◎ | ◎ | ○ | ◎ | ◎ | ◎ | ◎ |
| 5) Cleanability | ○ | ○ | ◎ | ◎ | X | ◎ | X |

After the tests, Preparation Examples 1-5 according to the present disclosure show higher cleanability with tepid water and good water resistance, as compared to Comparative Example 2 obtained by using a silicone coating agent. As judged from the overall result, Preparation Example 4 using Example 4 shows excellent water resistance and cleanability.

The present disclosure has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

INDUSTRIAL APPLICABILITY

The present disclosure provides a cosmetic composition which has excellent persistency and can be cleansed with ease. The cosmetic composition according to the present disclosure requires no makeup remover or oil cleanser and is removed from the skin simply by washing off it with water. The present disclosure also provides a non-aqueous dispersion used for such a simply water-cleanable cosmetic composition. The non-aqueous dispersion is applied to various cosmetic compositions to provide a cosmetic composition having high stability. Particularly, the mascara according to an embodiment of the present disclosure is removed perfectly with no need for a separate remover upon face-washing, while showing excellent persistency.

What is claimed is:

1. A method for preparing a non-aqueous dispersion, comprising the steps of:

S1) a first step of mixing and polymerizing at least one hydrophilic monomer selected from vinyl pyrrolidone and 2-hydroxyethyl acrylate with at least one hydrophobic monomer selected from n-butyl acrylate, and stearyl methacrylate to obtain a copolymer in a non-aqueous solvent; and S2) a second step of adding and polymerizing at least one hydrophilic monomer selected from acryl and vinyl compounds in the presence of the copolymer in the non-aqueous solvent from the first step to form the non-aqueous dispersion, wherein the copolymer obtained from the first step is used as a dispersion stabilizer for the hydrophilic monomer of the second step, and wherein a content of the hydrophilic monomer mixed in step S1) is 1-40 wt % based on a total weight of the monomers mixed in step S1), and a content of the hydrophobic monomer mixed in step S1) is 60-99 wt % based on the total weight of the monomers mixed in step S1), and wherein the non-aqueous solvent comprises $C_{10}$-$C_{16}$ hydrocarbon-containing oil.

2. The method for preparing a non-aqueous dispersion according to claim 1, wherein a hydrocarbon-containing oil and a radical initiator are added in step S1), and a radical initiator is added in step S2).

3. The method for preparing a non-aqueous dispersion according to claim 1, wherein the total content of the hydrophilic monomer in the non-aqueous dispersion is 50-90 wt %, and the total content of the hydrophobic monomer in the non-aqueous dispersion is 10-50 wt %.

4. The method for preparing a non-aqueous dispersion according to claim 1, wherein the content of the hydrophilic monomer mixed in step S1) is 5-25 wt % based on the total weight of the monomers mixed in step S1), and the content of the hydrophobic monomer mixed in step S1) is 75-95 wt % based on the total weight of the monomers mixed in step S1).

5. The method for preparing a non-aqueous dispersion according to claim 1, wherein the step S1) is carried out at 70-95° C. for 4-10 hours, and the step S2) is carried out at 70-95° C. for 5-24 hours.

6. The method for preparing a non-aqueous dispersion according to claim 1, wherein the hydrophilic monomer is added together with a radical initiator in the presence of the polymerized product of the S1) step.

7. The method for preparing a non-aqueous dispersion according to claim 2, wherein the radical initiator is added in an amount of 0.01-10 wt % based on the total weight of the monomers in the dispersion.

* * * * *